(12) United States Patent
Vance

(10) Patent No.: US 10,736,983 B2
(45) Date of Patent: Aug. 11, 2020

(54) AIR PURIFICATION COMPOSITION

(71) Applicant: Margaret Vance, Humble, TX (US)

(72) Inventor: Margaret Vance, Humble, TX (US)

( * ) Notice: Subject to any disclaimer, the term of this patent is extended or adjusted under 35 U.S.C. 154(b) by 0 days.

(21) Appl. No.: 16/161,501

(22) Filed: Oct. 16, 2018

(65) Prior Publication Data

US 2019/0111170 A1 Apr. 18, 2019

Related U.S. Application Data

(60) Provisional application No. 62/573,230, filed on Oct. 17, 2017.

(51) Int. Cl.
| | | |
|---|---|---|
| *A61L 9/012* | (2006.01) | |
| *A61L 9/013* | (2006.01) | |
| *A61K 8/96* | (2006.01) | |
| *A61L 9/04* | (2006.01) | |
| *A61L 9/14* | (2006.01) | |

(52) U.S. Cl.
CPC ............... *A61L 9/012* (2013.01); *A61K 8/96* (2013.01); *A61L 9/013* (2013.01); *A61L 9/14* (2013.01); *A61K 2800/77* (2013.01); *A61L 9/04* (2013.01); *A61L 2209/21* (2013.01)

(58) Field of Classification Search
CPC . A61L 2209/21; A61L 9/013; A61K 2800/77; A61K 8/97
See application file for complete search history.

(56) References Cited

U.S. PATENT DOCUMENTS

| | | |
|---|---|---|
| 6,280,751 B1 | 8/2001 | Fletcher et al. |
| 2005/0019269 A1 | 1/2005 | Marks et al. |
| 2008/0038219 A1 | 2/2008 | Mosbaugh et al. |
| 2010/0303935 A1 | 12/2010 | Squires |
| 2011/0274643 A1* | 11/2011 | Yontz ............... A61K 8/25 424/76.1 |
| 2017/0136076 A1 | 5/2017 | Soman et al. |

* cited by examiner

*Primary Examiner* — Kortney L. Klinkel
(74) *Attorney, Agent, or Firm* — Boudwin Intellectual Property; Daniel Boudwin

(57) ABSTRACT

An air purification composition. The air purification composition includes patchouli, lavender, lemon, lemongrass, rosewood, white camphor and tea tree. The air purification composition has the form of a fluid concentrate which can be used by itself or in combination with other ingredients. The air purification composition may be utilized in a targeted area to improve the air quality and scent of the air.

11 Claims, No Drawings

AIR PURIFICATION COMPOSITION

CROSS REFERENCE TO RELATED APPLICATIONS

This application claims the benefit of U.S. Provisional Application No. 62/573,230 filed on Oct. 17, 2017. The above identified patent application is herein incorporated by reference in its entirety to provide continuity of disclosure.

BACKGROUND OF THE INVENTION

The present invention relates to a composition of natural ingredients. More specifically, the present invention provides a composition that purifies air in a targeted location such as to provide pure air to individuals with weakened immune systems.

Many people suffer from medical conditions that result in a weakened or compromised immune system. Individuals who have immune system deficiencies may be at an increased risk of contracting an illness from an airborne bacteria, virus or allergen. The risks are further enhanced in high traffic areas, such as shopping centers, airplanes and transportation centers.

Additionally, many individuals suffer from sleep disorders, such as insomnia, that can lead to obesity, high blood sugar, and inflammation. Furthermore, many individuals are subjected to high stress environments, which can lead to sleep loss that may cause further health risks to the individual, including an increased risk of heart attack or stroke. Therefore, there is a defined need in the known art for an air purification composition that can provide an improved air quality that eliminates odors for the benefit of individuals with immune system deficiencies, stress or sleeping disorders.

SUMMARY OF THE INVENTION

In view of the foregoing disadvantages inherent in the known types of air purification compositions now present in the known art, the present invention provides an air purification system wherein the same can be utilized for providing convenience for the user when purifying the air in a targeted location.

One embodiment of the air purification composition is a mixture of components, the composition of which comprises patchouli, lavender, lemon, lemongrass, rosewood, white camphor, cinnamon leaf and tea tree.

An object of the present invention is to provide a composition which can be mixed into a volume of distilled water and placed into a spray bottle, such that the composition can be sprayed into a targeted area.

Another object of the present invention is to provide a composition which can be mixed into a volume of lotion, such that the composition can be rubbed onto an individual's skin.

Other objects, features and advantages of the present invention will become apparent from the following detailed description.

DETAILED DESCRIPTION OF THE INVENTION

Although the characteristic features of this invention will be particularly pointed out in the claims, the invention itself and manner in which it may be made and used may be better understood upon review of the following detailed description.

The present invention provides a composition for freshening the air in a targeted location. In one embodiment, the composition has the form of a fluid concentrate. The mixture is composed of various extracts and oils. Some components of the mixture provide a pleasant scent. Other components provide antibacterial properties to the mixture.

The mixture embodiment of the air purification composition includes patchouli, lavender, lemon, lemongrass, rosewood, white camphor, cinnamon leaf, and tea tree. In one embodiment, the patchouli is an extracted oil from a patchouli plant. The extraction of patchouli oil is primarily to procure two chemical compounds: patchoulol and norpatchoulenol. Patchouli oil is primarily utilized for its pleasant aroma. In one embodiment, the air purification composition comprises patchouli in a range of 23.3% by volume to 30% by volume.

In another embodiment, the lavender is an extracted oil from a lavender plant. Lavender oil is primarily utilized because it provides both antiseptic properties and anti-inflammatory properties. Additionally, lavender oil may be utilized for its pleasant aroma. In one embodiment, the air purification composition comprises lavender within a range of 15% to 17.4% by volume.

In one embodiment, the lemon is an extracted oil from at least one of a lemon peel or a lemon juice. Lemon oil is utilized primarily for its deodorizing properties. Furthermore, lemon oil has aromatherapeutic properties that may contribute to relaxation in many individuals. In one embodiment, the air purification composition comprises lemon within a range of 15% to 17.4% by volume. In another embodiment, the volume of lemon is equivalent to the volume of lavender.

In another embodiment, the lemongrass is an extracted oil from a lemongrass plant. Lemongrass oil is utilized primarily for its anti-fungal, antiseptic and anti-inflammatory properties. Furthermore, lemongrass oil provides aromatherapeutic properties as it produces a pleasant aroma. In one embodiment, the air purification composition comprises lemongrass within a range of 9.3% to 10% by volume.

In a further embodiment, the white camphor is an extracted oil from at least one of a wood portion or a leaf of a camphor laurel. White camphor oil is primarily utilized for its scent. Additionally, white camphor oil has anti-inflammatory properties. In one embodiment, the air purification composition comprises white camphor within a range of 9.3% to 10% by volume. In another embodiment, the volume of white camphor is equivalent to the volume of lemongrass.

In yet another embodiment, rosewood is an extracted oil from the aniba rosaedora tree. Rosewood oil is primarily utilized for its scent. Furthermore, rosewood provides analgesic and antiseptic properties when utilized as an oil extraction. In one embodiment, the air purification composition comprises rosewood within a range of 8% to 9.3% % by volume. In another embodiment, the volume of rosewood is equivalent to at least one of the volume of white camphor and the volume of lemongrass.

In another embodiment, the cinnamon leaf is an extracted oil from a leaf of a cinnamon plant. Cinnamon leaf oil is primarily utilized for its scent and is used in aromatherapy to reduce stress. However, cinnamon leaf oil also has antiseptic properties. In one embodiment, the air purification composition comprises cinnamon leaf within a range of 6% to 7% by volume.

In one embodiment, the tea tree is an extracted oil from a leaf of a tea tree. Tea tree oil is primarily utilized for its scent. In one embodiment, the air purification composition comprises tea tree within a range of 6% to 7% by volume. In another embodiment, the volume of tea tree is equivalent to the volume of cinnamon leaf.

One example of the above described air purification composition consists of 30% by volume patchouli, 15% by volume lavender, 15% by volume lemon, 10% by volume lemongrass, 10% by volume white camphor, 8% by volume rosewood, 6% by volume cinnamon leaf and 6% by volume tea tree.

Another example of the above described air purification composition consists of 23.3% by volume patchouli, 17.4% by volume lavender, 17.4% by volume lemon, 9.3% by volume lemongrass, 9.3% by volume rosewood, 9.3% by volume white camphor, 7% by volume cinnamon leaf, and 7% by volume tea tree.

In use, the air purification composition can be used by itself, or can be combined with additional ingredients to accomplish various objects. For example, the air purification composition can be used as, or in combination with, an aroma spray, a lotion, a candle, a soap, a bath salt, an air diffuser, and a wick diffuser. As an aroma spray, the air purification composition can be combined with distilled water in a ratio of 5 millimeters of air purification composition and 1.5 liters of distilled water. The mixture can be placed into a spray bottle, wherein the mixture can be used as an aroma spray.

Furthermore, as a lotion, the air purification composition can be mixed with a lotion, such as a premium lotion, an organic lotion, or a combination thereof at a ratio of 5 teaspoons of air purification composition to 2 gallons of the lotion. The lotion can be applied to the skin of an individual such as to receive the benefits of the air purification composition.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An air purification composition, comprising a mixture of natural ingredients comprising:
    patchouli;
    lavender;
    lemon;
    lemongrass;
    white camphor;
    rosewood;
    cinnamon leaf; and
    tea tree;
    wherein the mixture of natural ingredients is mixed into a volume of lotion at a ratio of 1 teaspoon to 2 gallons.

2. The air purification composition of claim 1, wherein an amount of patchouli in the mixture of natural ingredients is a range of 23.3% to 30% by volume.

3. The air purification composition of claim 1, wherein an amount of lavender in the mixture of natural ingredients is a range of 15% to 17.4% by volume.

4. The air purification composition of claim 1, wherein an amount of lemon in the mixture of natural ingredients is a range of 15% to 17.4% by volume.

5. The air purification composition of claim 1, wherein an amount of lemongrass in the mixture of natural ingredients is in a range of 9.3% to 10% by volume.

6. The air purification composition of claim 1, wherein an amount of white camphor in the mixture of natural ingredients is a range of 9.3% to 10% by volume.

7. The air purification composition of claim 1, wherein an amount of rosewood in the mixture of natural ingredients is a range 8% to 9.3% by volume.

8. The air purification composition of claim 1, wherein an amount of cinnamon leaf in the mixture of natural ingredients is a range of 6% to 7% by volume.

9. The air purification composition of claim 1, wherein an amount of tea tree in the mixture of natural ingredients is a range of 6% to 7% by volume.

10. An air purification composition, comprising: a mixture of natural ingredients consisting of:
    30% patchouli by volume;
    15% lavender by volume;
    15% lemon by volume;
    10% lemongrass by volume;
    10% white camphor by volume;
    8% rosewood by volume;
    6% cinnamon leaf by volume; and
    6% tea tree by volume;
    wherein the mixture of natural ingredients is mixed into a volume of lotion at a ratio of 1 teaspoon to 2 gallons.

11. An air purification composition, comprising: a mixture of natural ingredients consisting of:
    23.3% patchouli by volume;
    17.4% lavender by volume;
    17.4% lemon by volume;
    9.3% lemongrass by volume;
    9.3% rosewood by volume;
    9.3% white camphor by volume;
    7% cinnamon leaf by volume; and
    7% tea tree by volume;
    wherein the mixture of natural ingredients is mixed into a volume of lotion at a ratio of 1 teaspoon to 2 gallons.

* * * * *